(12) United States Patent
Cho et al.

(10) Patent No.: US 9,463,152 B2
(45) Date of Patent: Oct. 11, 2016

(54) MAKE-UP COSMETIC COMPOSITION CONTAINING MQ SILICONE RESIN AND PROPYL SILSESQUIOXANE RESIN

(71) Applicant: AMOREPACIFIC CORPORATION, Seoul (KR)

(72) Inventors: Hye Jeon Cho, Yongin-si (KR); Kyung Nam Kim, Yongin-si (KR); Kyung Ho Choi, Yongin-si (KR); Yeong Jin Choi, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 14/398,013

(22) PCT Filed: Apr. 22, 2013

(86) PCT No.: PCT/KR2013/003412
§ 371 (c)(1),
(2) Date: Oct. 30, 2014

(87) PCT Pub. No.: WO2013/165113
PCT Pub. Date: Nov. 7, 2013

(65) Prior Publication Data
US 2015/0132246 A1    May 14, 2015

(30) Foreign Application Priority Data

Apr. 30, 2012 (KR) .......................... 10-2012-0045406
Apr. 19, 2013 (KR) .......................... 10-2013-0043591

(51) Int. Cl.
*A61K 8/891* (2006.01)
*A61Q 1/02* (2006.01)
*A61Q 19/00* (2006.01)

(52) U.S. Cl.
CPC .............. *A61K 8/891* (2013.01); *A61Q 1/02* (2013.01); *A61Q 19/00* (2013.01); *A61K 2800/594* (2013.01); *A61Q 19/007* (2013.01)

(58) Field of Classification Search
None
See application file for complete search history.

(56) References Cited

U.S. PATENT DOCUMENTS

| 6,423,322 | B1 | 7/2002 | Fry | |
| 2002/0031488 | A1 | 3/2002 | Kanji et al. | |
| 2007/0166271 | A1* | 7/2007 | Gordon | A61K 8/585 424/70.122 |

FOREIGN PATENT DOCUMENTS

| JP | 3631941 | 12/2004 |
| KR | 10-2007-0004617 | 1/2007 |
| KR | 10-2007-0121059 | 12/2007 |
| KR | 10-2009-0054540 | 6/2009 |

OTHER PUBLICATIONS

International Search Report for PCT/KR2013/003412, mailed Jul. 25, 2013.
Foreign-language Written Opinion of the International Searching Authority for PCT/KR2013/003412, mailed Jul. 25, 2013.

* cited by examiner

*Primary Examiner* — Jennifer Berrios
(74) *Attorney, Agent, or Firm* — Nixon & Vanderhye P.C.

(57) ABSTRACT

The present invention relates to a make-up cosmetic composition containing MQ silicone resin and propyl silsesquioxane resin, and, more specifically, relates to a make-up cosmetic composition which contains MQ silicone resin and propyl silsesquioxane resin, gives an outstanding moisturizing impression and is free from any pulling phenomenon.

6 Claims, 1 Drawing Sheet

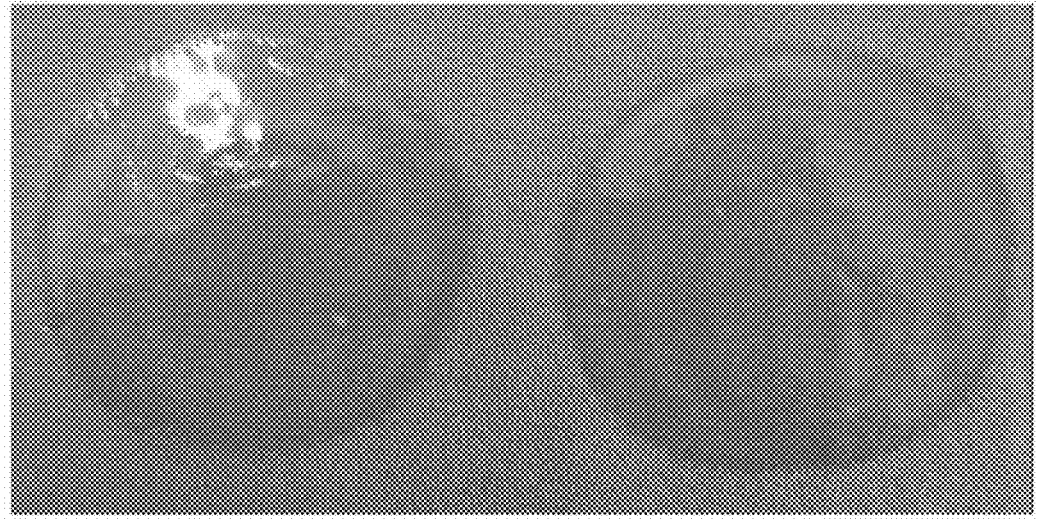
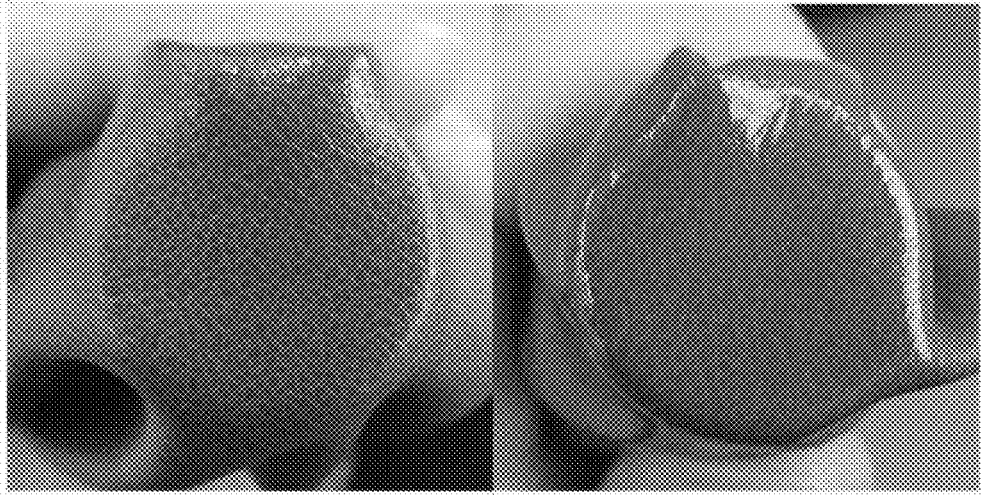

MAKE-UP COSMETIC COMPOSITION CONTAINING MQ SILICONE RESIN AND PROPYL SILSESQUIOXANE RESIN

This application is the U.S. national phase of International Application No. PCT/KR2013/003412, filed 22 Apr. 2013, which designated the U.S. and claims priority to KR Application No. 10-2012-0045406, filed 30 Apr. 2012, and KR Application No. 10-2013-0043591, filed 19 Apr. 2013, the entire contents of each of which are hereby incorporated by reference.

TECHNICAL FIELD

The present invention relates to a makeup cosmetic composition containing, as active ingredients, MQ silicone resin and propyl silsesquioxane resin, which make the skin moist without drying or pulling of the skin.

BACKGROUND ART

With the passage of time after application of a makeup cosmetic composition such as a foundation to the skin, the removal of makeup by the sweat and sebum secreted from the skin is observed. In a method for maintaining a makeup layer for a long time, MQ silicone resin can be used to improve the maintenance of a pigment or other active materials on the skin, but cosmetic compositions comprising MQ silicon resin have the problem of causing drying and pulling of the skin. For this reason, there is a need for a siloxane resin that exhibits the maintenance similar to that of MQ silicone resin used in current cosmetic formulations and that exhibits an excellent moisturizing sensation and does not cause pulling of the skin.

DISCLOSURE

Technical Problem

As used herein, "pulling of the skin" refers to a phenomenon that can easily occur when moisturization of the skin or the supply of moisture to the skin is insufficient. The present inventors have found that MQ silicone resin and propyl silsesquioxane resin have excellent effects of preventing pulling of the skin and moisturizing the skin, thereby completing the present invention.

Therefore, it is an object of the present invention to provide a makeup cosmetic composition containing MQ silicone resin and propyl silsesquioxane resin, which exhibit an excellent moisturizing sensation and do not cause pulling of the skin.

Technical Solution

The present invention is directed to a makeup cosmetic composition containing, as active ingredients, MQ silicone resin and propyl silsesquioxane resin, which make the skin moist without drying or pulling of the skin.

Advantageous Effects

A makeup cosmetic composition according to the present invention can form a long-lasting makeup layer and maintain the skin in a moist state without drying or pulling of the skin.

DESCRIPTION OF DRAWINGS

FIG. 1 is a set of photographs showing a state in which compositions of Comparative Example 4 and Example 2 were applied to synthetic leather (FIG. 1a) and a state in which the leather was pulled after 15 minutes of drying following application of the compositions (FIG. 1b).

BEST MODE

The present invention relates to a makeup cosmetic composition containing, as active ingredients, MQ silicone resin and propyl silsesquioxane resin, which make the skin moist without drying or pulling of the skin. The present invention will be described in further detail.

In an embodiment of the present invention, the MQ silicone resin is selected from among an M unit represented by $(R^1_3SiO_{1/2})_a$ and a Q unit represented by $(SiO_{4/2})_b$, wherein the $R^1$ groups may independently be an alkyl group having 1 to 8 carbon atoms or an aryl group. Examples of the alkyl group include methyl, ethyl, propyl, butyl, pentyl and hexyl, and examples of the aryl group include phenyl, naphthyl, benzyl, tolyl, xylyl and xenyl. a and b are integers greater than 0, and the ratio of a/b is 0.5-1.5. The MQ silicone resin may further contain at least one of a D unit and a T unit, provided that at least 80 mole % or at least 90 mole % of the MQ silicone resin consists of the M and Q units. The MQ silicone resin may be, for example, trimethylsiloxysilicate, but is not limited thereto.

In an embodiment of the present invention, the propyl silsesquioxane resin comprises a T unit, represented by $R^2SiO_{3/2}$, in an amount of at least 80 mole % based on the total moles of the propyl silsesquioxane resin. Herein, the $R^2$ groups are independently an alkyl group having 1 to 8 carbon atoms or an aryl group, and at least 40 mole % of $R^2$ is propyl. The propyl silsesquioxane resin may further contain one or more from the group consisting of M, D and Q units, provided that at least 80 mole % of the propyl silsesquioxane resin consists of the T units. The propyl silsesquioxane resin may be, for example, polypropylsilsesquioxane.

The M unit, D unit, T unit and Q unit are silicone polymer units that may be represented by the following formula 1:

Formula 1

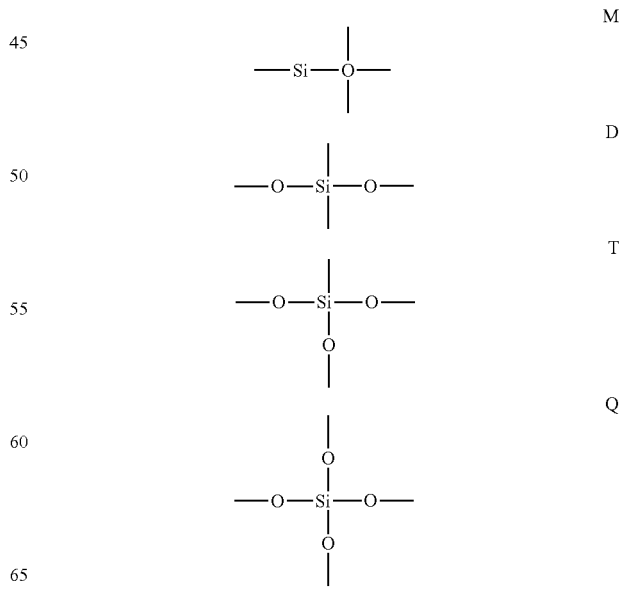

In an embodiment of the present invention, the MQ silicone resin may be contained in an amount of 0.01-30 wt %, and preferably 0.01-10 wt %, based on the total weight of the composition. If the content of the MQ silicone resin in the composition is less than 0.01 wt %, it will not significantly contribute to skin moisturization, and if the content of the MQ silicone resin is more than 30 wt %, it will cause severe pulling of the skin.

In an embodiment of the present invention, the propyl silsesquioxane resin may be contained in an amount of 0.01-30 wt %, and preferably 0.01-10 wt %, based on the total weight of the composition. If the content of the propyl silsesquioxane resin in the composition is less than 0.01 wt %, it will not significantly contribute to skin moisturization, and if the content of the propyl silsesquioxane resin is more than 30 wt %, the touch feeling of the composition can become heavy.

In an embodiment of the present invention, the composition may contain the MQ silicone resin and the propyl silsesquioxane resin at a weight ratio of 1:150 to 150:1, and preferably 1:80 to 80:1. If the weight ratio is out of the above range, the touch feeling of the composition can be reduced.

A composition according to an embodiment of the present invention may contain a cosmetically or dermatologically acceptable medium or base. It may preferably be prepared into any formulation suitable for topical application and may be of a type selected from the group consisting of a water-in-oil type, an oil-in-water type and an oil dispersion type. Also, it can be provided in the form of suspension, microemulsion, microcapsule, microgranule or ionic (liposome) or non-ionic vesicular dispersion. In addition, it can be provided in the form of cream, skin toner, lotion, powder, ointment, spray or conceal stick. In addition, it can be used in the form of foam or as an aerosol composition further containing a compressed propellant. These compositions can be prepared according to any conventional method known in the art.

A makeup cosmetic composition according to an embodiment of the present invention may contain additives that are generally used in the cosmetic or skin science field, as long as these additives do not impair the purpose of the present invention. Examples of these additives include fatty substances, organic solvents, solubilizing agents, thickeners, gelling agents, softeners, antioxidants, suspending agents, stabilizers, foaming agents, aromatic substances, surfactants, water, ionic or non-ionic emulsifying agents, fillers, sequestering agents, chelating agents, preservatives, vitamins, blockers, moisturizing agents, essential oil, dyes, pigments, hydrophilic or hydrophobic activators, lipid vesicles, or other components, which are generally used in cosmetics. The additives are contained in amounts that are generally used in the cosmetic or skin science field. Further, the composition of the present invention may contain a skin absorption-promoting material in order to increase the effects of improving skin conditions Mode for Invention Hereinafter, the present invention will be described in further detail with reference to examples. It will be obvious to those skilled in the art that these examples are for illustrative purposes only and are not intended to limit the scope.

Comparative Examples 1 to 3 and Example 1

According to the components and contents shown in Table 1 below, compositions of Comparative Examples 1 to 3 and Example 1 were prepared.

TABLE 1

| | Components (wt %) | Comp. Example 1 | Comp. Example 2 | Comp. Example 3 | Example 1 |
|---|---|---|---|---|---|
| Oil phase | Ethylhexyl methoxycinnamate | 5.00 | 5.00 | 5.00 | 5.00 |
| | Cyclopentasiloxane | 25.00 | 15.00 | 15.00 | 15.00 |
| | Methyl trimethicone | 5.00 | 5.00 | 5.00 | 5.00 |
| | Phenyl trimethicone | 4.00 | 4.00 | 4.00 | 4.00 |
| | Trimethylsiloxysilicate | — | 10.00 | — | 5.00 |
| | Polypropyl silsesquinoxane | — | — | 10.00 | 5.00 |
| | PEG-10 dimethicone | 3.50 | 3.50 | 3.50 | 3.50 |
| | Cetyl PEG/PPG-10/1 dimethicone | 1.00 | 1.00 | 1.00 | 1.00 |
| | Disteardimonium hectorite | 1.50 | 1.50 | 1.50 | 1.50 |
| Powdery materials | Titanium oxide surface treated with alkylsilane | 8.00 | 8.00 | 8.00 | 8.00 |
| | Iron oxide yellow surface treated with alkylsilane | 0.60 | 0.60 | 0.60 | 0.60 |
| | Iron oxide red surface treated with alkylsilane | 0.20 | 0.20 | 0.20 | 0.20 |
| | Iron oxide black surface treated with alkylsilane | 0.15 | 0.15 | 0.15 | 0.15 |
| | Polymethylmethacrylate | 1.05 | 1.05 | 1.05 | 1.05 |
| Water phase | Purified water | 38.70 | 38.70 | 38.70 | 38.70 |
| | Butylene glycol | 5.00 | 5.00 | 5.00 | 5.00 |
| | Sodium chloride | 1.00 | 1.00 | 1.00 | 1.00 |

Preparation Method

1) The above-described oil-phase components and powdery materials were mixed with one another to form a dispersion.

2) The water-phase components were mixed with one another.

3) The mixture of 2) was added slowly to the mixture of 1), and then stirred to form an emulsion.

4) The mixture was completely degassed, thereby preparing a water-in-oil type makeup cosmetic composition.

Test Example 1

Sensory Evaluation of Makeup Cosmetic Compositions

Each of the compositions of Comparative Examples 1 to 3 and Example 1 was applied to the face of each of 20 women aged 25-39 years old, and after 12 hours, two items (moist sensation and no skin pulling) were evaluated by questionnaire. Each of the items was evaluated on a 5-point scale, and a better effect was given a higher score. The averages of the scores are shown in Table 2 below.

TABLE 2

| Evaluation item | Comparative Example 1 | Comparative Example 2 | Comparative Example 3 | Example 1 |
|---|---|---|---|---|
| Moist sensation without drying | 1.4 | 1.7 | 1.9 | 4.3 |
| No skin pulling | 1.3 | 1.5 | 1.8 | 4.2 |

As can be seen from the results in Table 2 above, the composition of Comparative Example 2 containing the MQ silicone resin alone showed low satisfaction in terms of drying or pulling, and the composition of Comparative Example 3 containing the polypropyl silsesquioxane resin alone also showed low satisfaction in terms of drying or pulling. However, the composition of Example 1 containing both the MQ silicone resin and the polypropyl silsesquioxane resin showed high satisfaction in terms of all the evaluation items. Thus, it can be seen that the composition of the present invention, which contains both the MQ silicone resin and the polypropyl silsesquioxane resin, exhibits an excellent moisturizing sensation and the effect of reducing skin pulling.

Test Example 2

Evaluation of Reduction in Drying and Pulling of the Skin

In order to confirm whether drying and pulling of the skin decrease when both the MQ silicone resin and the polypropyl silsesquioxane resin according to the present invention are used, the following test was performed. According to the compositions shown in Table 3 below, powdery components were dispersed in a silicone resin solution. The solution was applied to artificial leather to a thin thickness, and then dried for 15 minutes. The dried synthetic leather was physically stimulated by pulling it in four directions 30 times for each direction, and the surface of the synthetic leather having the solution applied thereto was observed. FIG. 1 shows a photograph of the surface of the synthetic leather.

TABLE 3

| Components (wt %) | Comparative Example 4 | Example 2 |
|---|---|---|
| Trimethylsiloxysilicate | 95 | 47.5 |
| Polypropyl silsesquinoxane | — | 47.5 |
| Titanium oxide surface treated with alkylsilane | 4.00 | 4.00 |
| Iron oxide yellow surface treated with alkylsilane | 0.30 | 0.30 |
| Iron oxide red surface treated with alkylsilane | 0.10 | 0.10 |
| Iron oxide black surface treated with alkylsilane | 0.07 | 0.07 |
| Polymethylmethacrylate | 0.53 | 0.53 |

As can be seen from the results in FIG. 1, when the surface of the synthetic leather was observed after the synthetic leather was stimulated, it could be seen that, in the case of the composition of Comparative Example 4 containing trimethylsiloxysilicate alone, the surface of the synthetic leather was dried and torn. In other words, it can be expected that the composition of Comparative Example 4 will cause pulling of the skin due to its low flexibility. However, it could be seen that the composition of Example 2 containing trimethylsiloxysilicate and polypropyl silsesquioxane at a weight ratio of 1:1 formed a moist flexible layer without tearing or splitting of the surface of the synthetic leather.

INDUSTRIAL APPLICABILITY

The makeup cosmetic composition according to the present invention contains, in addition to MQ silicone resin, a siloxane resin exhibiting an excellent moisturizing sensation without pulling of the skin, and thus can maintain the skin in a moist state without drying and pulling of the skin.

The invention claimed is:

1. A method of increasing skin moisturization or reducing skin pulling, the method comprising applying a cosmetic composition to skin of a subject in need of skin moisturization or reduction of skin pulling, the composition containing MQ silicone resin and propyl silsesquioxane resin as an effective ingredient, wherein the MQ silicone resin comprises a siloxy unit, selected from an M unit represented by $(R^1_3SiO_{1/2})_a$ and a Q unit represented by $(SiO_{4/2})_b$, in an amount of 80 mole % or more based on the total moles of the MQ silicone resin, in which the $R^1$ groups are independently an alkyl group having 1 to 8 carbon atoms or an aryl group, and a and b are integers greater than 0;

wherein the propyl silsesquioxane resin comprises a T unit, represented by $R^2SiO_{3/2}$, in an amount of 80 mole % based on the total moles of the propyl silsesquioxane resin, in which the $R^2$ groups are independently an alkyl group having 1 to 8 carbon atoms or an aryl group, and 40 mole % or more of $R^2$ is propyl;

wherein the MQ silicone resin and the propyl silsesquioxane resin are contained at a weight ratio of 1:1; and wherein the composition further contains as an additive:
polymethylmethacrylate; and
titanium oxide surface treated with alkylsilane or a mixture of titanium oxide surface treated with alkylsilane and iron oxide surface treated with alkylsilane;
wherein the iron oxide is yellow, red or black.

2. The method of claim 1, wherein 80 mole % or more of the MQ silicone resins consists of the M and Q units.

3. The method of claim 1, wherein the propyl silsesquioxane resin further contains one or more selected from the group consisting of M, D and Q units.

4. The method of claim 1, wherein the MQ silicone resin is contained in an amount of 0.01-30 wt % based on the total weight of the composition.

5. The method of claim 1, wherein the propyl silsesquioxane resin is contained in an amount of 0.01-30 wt % based on the total weight of the composition.

6. The method of claim 1, wherein the composition is of a type selected from the group consisting of a water-in-oil type, an oil-in-water type and an oil dispersion type.

* * * * *